(12) United States Patent
Vollmueller et al.

(10) Patent No.: US 6,197,967 B1
(45) Date of Patent: Mar. 6, 2001

(54) PROCESS FOR THE PREPARATION OF PARAOXADIAZOLYPHENYLBORONIC ACIDS

(75) Inventors: Frank Vollmueller, Mainz; Steffen Haber, Koenigstein; Andreas Meudt, Floersheim-Weilbach; Antje Noerenberg; Stefan Scherer, both of Buettelborn, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/460,664

(22) Filed: Dec. 13, 1999

(30) Foreign Application Priority Data

Dec. 15, 1998 (DE) .............................................. 198 57 765

(51) Int. Cl.$^7$ .............................. C07D 273/02; C07F 5/04
(52) U.S. Cl. ........................ 548/110; 558/286; 558/287; 558/289
(58) Field of Search ............................ 548/110; 558/286, 558/287, 289

(56) References Cited

U.S. PATENT DOCUMENTS 6,037,505 * 3/2000 Quallich ................................ 568/881

OTHER PUBLICATIONS

Torssell, Kurt, Arylboronic Acids, Arkiv Kemi, 10, 473–82, 1957.*
UK Search Report.
Chemical Abstract 121:122228 and JP 05239069 A2 (Canon), see compound with Registry No. 156932–96–6.
Chemical Abstract 118:244752 and JP 05032675 A2 (Showa Shell Sekiyu), see compound with Registry No. 147442–15–7.

* cited by examiner

Primary Examiner—Floyd D. Higel
Assistant Examiner—Sonya N. Wright
(74) Attorney, Agent, or Firm—Scott E. Hanf

(57) ABSTRACT

Compounds of the formula (I)

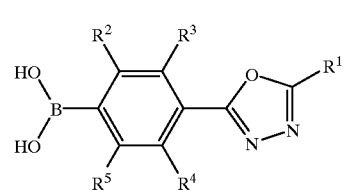

are prepared by reacting a compound of the formula (V)

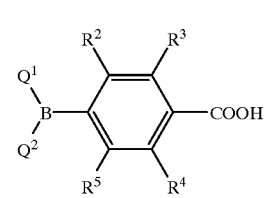

with a compound of the formula (X)

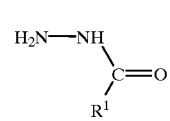

and hydrolyzing the product; or converting the compound of the formula (V) into the hydrazide, and cyclizing and hydrolyzing the latter to give the oxadiazole.

para-Oxadiazolylphenylboronic acids are valuable precursors for active ingredients.

10 Claims, No Drawings

PROCESS FOR THE PREPARATION OF PARAOXADIAZOLYPHENYLBORONIC ACIDS

CROSS-REFERENCE TO RELATED APPLICATION

The present invention is described in the German priority application No. 198 57 765.6, filed Dec. 15, 1998, which is hereby incorporated by reference as is fully disclosed herein.

BACKGROUND OF THE INVENTION para-Oxadiazolylphenylboronic acids are of considerable industrial importance as precursors for active ingredients, in particular as precursors for correspondingly substituted biphenyl derivatives, which are used as AT (II) antagonists, or as precursors for liquid-crystalline compounds, as liquid crystals or as a constituent of liquid-crystalline mixtures. Phenylboronic acids can be coupled to haloaromatic compounds with catalysis by transition metals with the aid of methods described in the literature, to give biphenyl derivatives (N. Miyaura et al., Tetrahedron Lett., 3437 (1979); A. L. Casalnuovo et al., J. Amer. Chem. Soc. 112, 4324 (1990)).

SUMMARY OF THE INVENTION

Owing to the interest in this class of compounds, there is a need for an economical and technically simple synthesis of 4-(2'-oxadiazolyl)-phenylboronic acids.

DESCRIPTION OF THE PREFERRED EMBODIMENTS

This object is achieved by a process for the preparation of a compound of the formula (I)

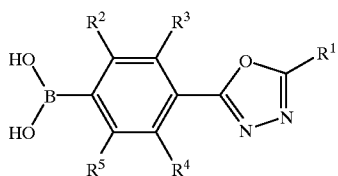

(I)

in which R' is hydrogen, $C_1$–$C_{12}$-alkyl, $C_3$–$C_{12}$-cycloalkyl, $C_2$–$C_{12}$-alkenyl, $C_2$–$C_{12}$-alkynyl, $C_1$–$C_{12}$-alkoxy, alkoxy-($C_1$–$C_{12}$-alkyl), alkoxy-($C_2$–$C_{12}$-alkenyl), alkoxy-($C_2$–$C_{12}$-alkynyl), acyloxy-($C_1$–$C_{12}$-alkyl), acyloxy-($C_2$–$C_{12}$-alkenyl), acyloxy-($C_2$–$C_{12}$-alkynyl), aryl, heteroaryl, OH, SH, F, Cl, Br, I or NR'R", where R' and R", independently of one another, are hydrogen, $C_1$–$C_{12}$-alkyl, $C_3$–$C_{12}$-cycloalkyl or aryl, $R^2$ to $R^5$, independently of one another, are hydrogen, $C_1$–$C_{12}$-alkyl, $C_2$–$C_{12}$-alkenyl, $C_2$–$C_{12}$-alkynyl, $C_3$–$C_{12}$-cycloalkyl, ($C_1$–$C_{12}$-)-alkoxy, ($C_1$–$C_{12}$)-acyloxy, O-phenyl, O-benzyl, aryl, heteroaryl, hydroxyl, fluorine, chlorine, bromine, iodine, nitro, CN, $SO_2R$ or SOR, where R is hydrogen, $C_1$–$C_4$-alkyl, aryl, chlorine or fluorine, or are $NH_2$, N(alkyl)$_2$, N[Si($C_1$–$C_4$-alkyl)$_3$]$_2$, $CF_3$, $CCl_3$, COO-($C_1$–$C_{12}$-alkyl), CO-($C_1$–$C_{12}$-alkyl), CO-phenyl, COO-phenyl, CHCHCOO-($C_1$–$C_2$-alkyl), PO-phenyl$_2$, PO-($C_1$–$C_8$-alkyl)$_2$ or PO$_3$($C_1$–$C_8$-alkyl)$_2$, or $R^2$ and $R^3$, and/or $R^4$ and $R^5$, together form an aliphatic or aromatic ring, wherein a compound of the formula (V)

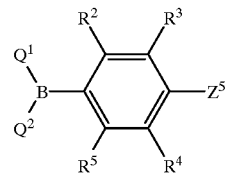

(V)

in which $Z^5$ is —COOH;

is reacted with a compound of the formula (X)

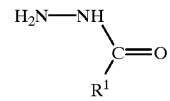

(X)

to give the compound of the formula (I')

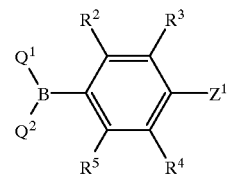

(I')

in which $Z^1$ is

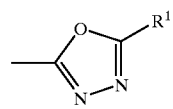

and the compound of the formula (I') is hydrolyzed to give the compound of the formula (I), or the compound of the formula (V) is firstly reacted with hydrazine to give a compound of the formula (II)

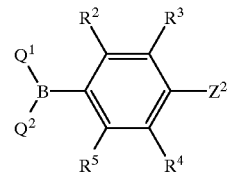

(II)

in which $Z^2$ is —CONHNH$_2$, and the compound of the formula (II) is cyclized and hydrolyzed; where $Q^1$ and $Q^2$ are each a radical of the formula —O-($C_1$–$C_{12}$)-alkyl, —O-($C_2$–$C_{12}$)-alkenyl, —O-($C_2$–$C_{12}$)-alkynyl, —O-aryl, —O-alkylaryl or —O—Si($C_1$–$C_4$-alkyl)$_3$; or $Q^1$, $Q^2$ and the adjacent boron atom form a cyclic boronic ester with the following alcohols: ($C_3$–$C_{12}$)-cycloalkane-1,2-diol, ($C_5$–$C_{12}$)-cycloalkene-1,2-diol, ($C_5$–$C_{12}$)-cycloalkane-1,3-diol, ($C_5$–$C_{12}$)-cycloalkene-1,3-diol or with alcohols of the formulae (Ia) to (If)

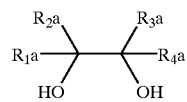

(Ia)

-continued

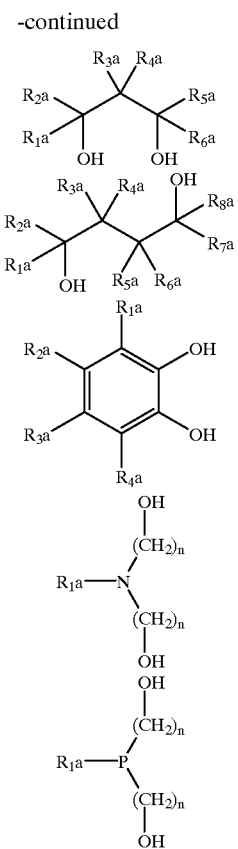

in which $R_1a$ to $R_8a$, independently of one another, are hydrogen, $C_1$–$C_{12}$-alkyl, $C_1$–$C_{12}$-hydroxyalkyl, $C_2$–$C_{12}$-alkenyl, $C_2$–$C_{12}$-alkynyl, $C_3$–$C_{12}$-cycloalkyl, ($C_1$–$C_{12}$)-alkoxy, ($C_1$–$C_{12}$)-acyloxy, O-phenyl, O-benzyl, aryl, heteroaryl, fluorine, chlorine, bromine, iodine, $NO_2$, CN, $SO_2R$, SOR, where R is as defined above, or are $NH_2$, $N(alkyl)_2$, $N[Si(C_1$–$C_4$-alkyl$)_3]_2$, $CF_3$, $CCl_3$, $CBr_3$, COO-($C_1$–$C_{12}$-alkyl), CO-($C_1$–$C_{12}$-alkyl), CO-phenyl, COO-phenyl, CHCHCOO-($C_1$–$C_{12}$-alkyl), PO-phenyl$_2$, PO-($C_1$–$C_8$-alkyl)$_2$ or $PO_3(C_1$–$C_8$-alkyl), and/or two adjacent radicals $R_1a$ to $R_8a$ together form an aliphatic or aromatic ring, and in which n is an integer from 2 to 12, or in which $Q^1$ and $Q^2$ together form a divalent radical of the formula (Ig)

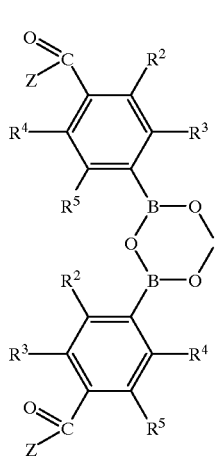

in which all radicals Z, in each case correspondingly, have one of the meanings of $Z^1$ to $Z^5$.

In the above definitions, alkyl is preferably $C_1$–$C_4$-alkyl, aryl is preferably phenyl, alkylaryl is preferably benzyl, alkoxy is preferably $C_1$–$C_4$-alkoxy, and aclyoxy is preferably $C_2$–$C_4$-acyloxy.

Preferred radicals $R^1$ are hydrogen, $C_1$–$C_4$-alkyl, $C_3$–$C_6$-cycloalkyl, $C_2$–$C_4$-alkenyl, phenyl, $NH_2$, OH, SH and $C_1$–$C_4$-alkoxy, in particular hydrogen, methyl, ethyl, phenyl and $NH_2$.

Preferred radicals $R^2$ to $R^5$ are hydrogen, methyl, ethyl, methoxy, ethoxy, fluorine, chlorine and bromine.

Preferred radicals $Q^1$ and $Q^2$ are —O-($C_1$–$C_6$)-alkyl, —O-($C_2$–$C_6$)-alkenyl, —O-($C_3$–$C_6$)-alkynyl, —O-phenyl, —O-benzyl, or $Q^1$ and $Q^2$, together with the boron atom, form a cyclic boronic ester with the following alcohols: ethylene glycol, 1,3-propanediol, 1,4-butanediol, 2,2-dimethylpropane-1,3-diol, pyrocatechol, pinacol, 2,3-dihydroxynaphthalene, diethanolamine, triethanolamine, trishydroxy-methylphosphine, 1,2-dihydroxycyclohexane, 1,3-dihydroxycyclopentane or 1,2-dihydroxycyclooctane.

The compound of the formula (V) can be obtained in a known manner, for example by oxidation of 4-tolylboronic acid using potassium permanganate (U.S. Pat. No. 5,631,364) and esterification with alcohols on which the radicals $Q^1$ and $Q^2$ are based in an inert organic solvent, for example methanol, ethanol, xylene or toluene. Methanol and ethanol can be used as inert solvents if, for example, the esterification is to be carried out using a diol, since this reacts significantly more quickly than methanol or ethanol.

The compound of the formula (V) is reacted with a compound of the formula (X), preferably formylhydrazine, acetohydrazide, propionohydrazide, benzohydrazide or semicarbazide in the presence or absence of an organic solvent which is inert toward the reaction participants, such as N,N-dimethylformamide, dimethylacetamide, N-methylpyrrolidone, dimethyl carbonate, sulpholane or dimethyl sulphoxide, and in the presence of an excess of a condensation agent, such as phosphorus oxychloride, phosphorus trichloride, polyphosphoric acid or acetic anhydride, at temperatures of from 50 to 250° C., preferably from 80 to 250° C., particularly preferably from 100 to 240° C.

The molar ratios between the compound of the formula (X) and the compound of the formula (V) are advantageously from 5:1 to 1:1 per carboxyl group in the compound of the formula (V).

The condensation agent is advantageously employed in a 1- to 5-fold molar excess per carboxyl group of the compound of the formula (V).

The resultant compound of the formula (I') can, for example, be precipitated by pouring the reaction mixture into aqueous bicarbonate solution and isolated by recrystallization from a suitable solvent, such as, for example, tetrahydrofuran, methylene chloride, chloroform or toluene, or hydrolyzed to the compound of the formula (I) without isolation. The hydrolysis of a compound of the formula (I') to the free boron acid can be carried out in the presence or absence of an organic solvent which is inert toward the reaction participants at temperatures of from 0 to 150° C., preferably from 5 to 100° C., particularly preferably from 20 to 80° C., by means of water or aqueous acids, such as, for example, aqueous ammonium chloride solution, dilute hydrochloric acid, dilute phosphoric acid, dilute sulphuric acid, dilute acetic acid, preferably with water or dilute acetic acid, heterogeneously, i.e. in the form of a suspension, or homogeneously by dissolving compounds of the formula (I') in suitable organic solvents. Examples of solvents which are suitable for this purpose are methanol, ethanol, propanol, cyclic and acyclic ethers, such as tetrahydrofuran, diethyl ether, methyl isobutyl ether, methyl isobutyl ketone, methyl ethyl ketone, toluene, o-, m-, p-xylene, N,N-dimethylformamide, dimethylacetamide, N-methylpyrrolidone, dimethyl carbonate, sulpholane or dimethyl sulphoxide, particularly preferably methanol, ethanol, tetrahydrofuran or toluene.

The compound of the formula (I) is insoluble in water and most organic solvents and can therefore be isolated as a precipitate. The compound of the formula (I) can be isolated from highly polar solvents, such as, for example, N-methylpyrrolidone or sulpholane, by removal of the solvent under reduced pressure.

In an alternative embodiment (Variant B), a compound of the formula (I') is prepared by firstly converting a compound of the formula (V) into the carbohydrazide of the formula (II) and cyclizing the latter to give the compound of the formula (I').

It is advantageous here to dissolve a compound of the formula (V) in an organic solvent which is inert toward the reaction participants, preferably in an alcohol, such as, for example, methanol, ethanol or propanol, or in a cyclic or acyclic ether, such as tetrahydrofuran, diethyl ether or methyl isobutyl ether, methyl isobutyl ketone, methyl ethyl ketone, toluene, o-, m- or p-xylene, N,N-dimethylformamide, dimethylacetamide, N-methylpyrrolidone, dimethyl carbonate, sulpholane or dimethyl sulphoxide, at temperatures of from 0 to 200° C., preferably from 50 to 180° C., particularly preferably from 60 to 130° C., and subsequently reacted with hydrazine hydrate in the presence of a suitable catalyst. Suitable catalysts are all common esterification catalysts, such as, for example, N,N-dimethylaminopyridine, dicyclohexylcarbodiimide, sulphuric acid, hydrochloric acid, phosphoric acid, toluenesulphonic acid, toluenesulphonyl chloride, trifluoroacetic acid, trifluoroacetic anhydride, boron trifluoride/diethyl ether complex, trimethylsilyl chloride, activated aluminium oxide or silica gel.

Hydrazine hydrate is advantageously employed in amounts of from 1 to 10 mol, preferably from 1 to 5 mol, in particular from 1 to 2 mol, per mole of carboxyl groups of the compound of the formula (V). The compound of the formula (II) can be isolated, for example, by removing the solvent by distillation followed by crystallization, for example from an alcohol.

The carbohydrazide of the formula (II) is cyclized in the presence or absence of an organic solvent which is inert toward the reaction participants, for example one used in the preceding process step, at temperatures of from 0 to 200° C., preferably from 50 to 180° C., particularly preferably from 80 to 150° C., with the aid of an orthocarboxylic ester, for example trimethyl orthoformate, triethyl orthoformate, tripropyl orthoformate, trimethyl orthoacetate, triethyl orthoacetate, tripropyl orthoacetate, trimethyl orthobenzoate or triethyl orthobenzoate, to give a compound of the formula (I'). The molar amount of orthocarboxylic ester per carbonylhydrazide group of the compound of the formula (II) is from about 1:1 to 10:1, preferably from 2:1 to 5:1.

The compound of the formula (II) can also be prepared by firstly converting the carboxyboronic acid of the formula (V) into a carboxylic acid halide of the formula (IV) (Variant C) or into a carboxylic ester of the formula (III) (Variant D), and reacting this with hydrazine hydrate, as described above, to give the carbohydrazide of the formula (II).

It is also possible firstly to prepare the carboxylic ester of the formula (III) from the carboxylic acid halide of the formula (IV), and then to convert this into the carbohydrazide (Variant A):

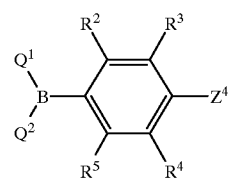

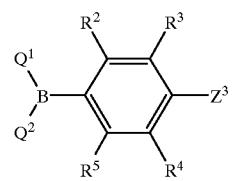

in which $Z^4$ is —COHal and $Z^3$ is —COOR$^6$, where Hal is Cl, Br or I, preferably Cl, and R$^6$ is $C_1$–$C_{12}$-alkyl, $C_2$–$C_{12}$-alkenyl, $C_2$–$C_{12}$alkynyl, $C_3$–$C_{12}$-cycloalkyl, $CF_3$, $CCl_3$, $CBr_3$, phenyl, benzyl, naphthyl, heteroaryl, $C_1$–$C_{12}$rhydroxyalkyl or $C_2$–$C_{12}$-hydroxyalkenyl, preferably methyl, ethyl, propyl, butyl, phenyl, benzyl or —CH$_2$CH$_2$OH.

In order to prepare the carboxylic acid halide of the formula (IV), the carboxylic acid of the formula (V) is reacted with a halogenating reagent, such as, for example, thionyl chloride, phosphorus(V) chloride or phosphorus(III) chloride, preferably thionyl chloride, at temperatures of from 0 to 200° C., preferably from 50 to 180° C., particularly preferably from 80 to 130° C., it being advantageous to employ a 1- to 5-fold molar excess, preferably a 1 - to 2-fold molar excess, of halogenating reagent per mole of carboxylic acid and per mole of carboxyl groups.

The carboxylic acid halide can be isolated by removing the solvent by distillation followed by precipitation, if necessary also after recrystallization, or converted into a compound of the formula (III) by reaction with a compound of the formula R$^6$OH, preferably methanol, ethanol, propanol, phenol or benzyl alcohol, in the presence or absence of an organic solvent which is inert toward the reaction participants, such as, for example, a cyclic or acyclic ether, such as tetrahydrofuran, diethyl ether, methyl isobutyl ether, methyl isobutyl ketone, methyl ethyl ketone, toluene, a xylene, DMF, DMA, NMP, dimethyl carbonate, sulpholane or DMSO, at temperatures of from 0 to 200° C., preferably from 50 to 180° C., particularly preferably from 80 to 130° C.

The reaction of the carboxylic acid halide of the formula (IV) and of the carboxylic ester of the formula (III) with hydrazine hydrate to give the carbohydrazide of the formula (II) can be carried out analogously to the above.

Schemes 1 and 2 below give an overview of process Variants A to E described above. Variant A proceeds via all intermediates (IV)-(III)-(II)-(I'). Particular preference is given to Variants A and D.

Scheme 1
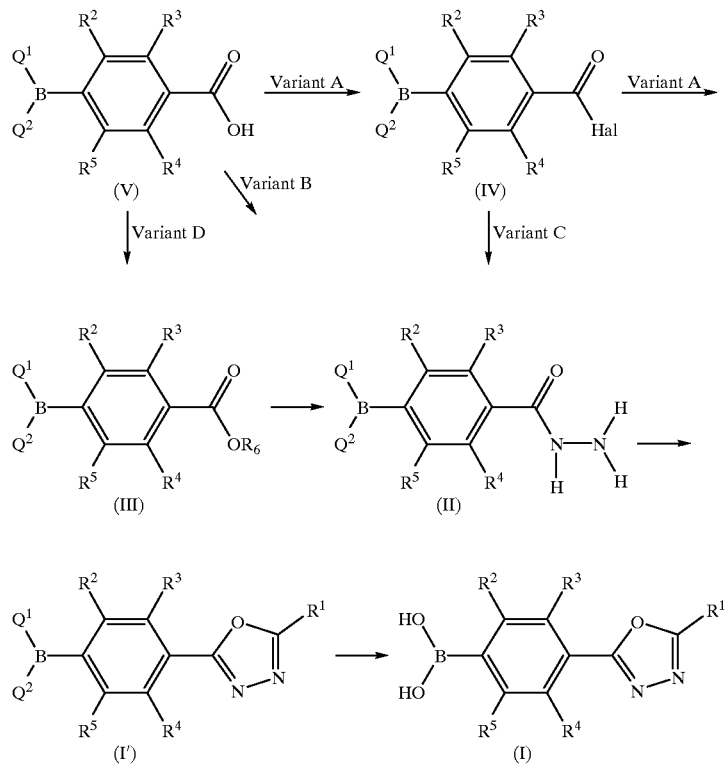
Scheme 2: Variant E
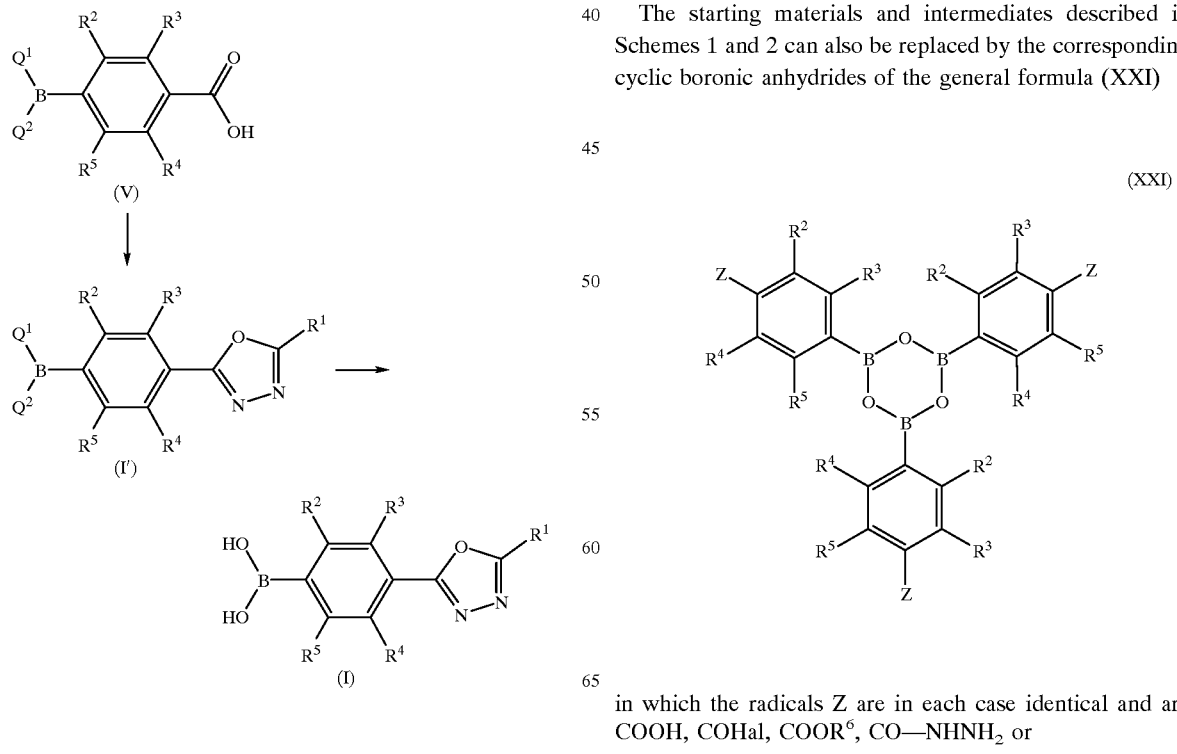
The starting materials and intermediates described in Schemes 1 and 2 can also be replaced by the corresponding cyclic boronic anhydrides of the general formula (XXI)
in which the radicals Z are in each case identical and are COOH, COHal, COOR$^6$, CO—NHNH$_2$ or

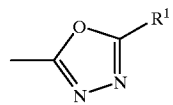

The respective reaction conditions can correspond to those described above for the respective reaction step, the molar amount employed of the respective cyclic boronic anhydride advantageously being about one third of the above amount described for the respective monomeric boronic acid derivatives.

Compounds of the formula (XXI) can be prepared by heating a monomeric boronic acid derivative of the formulae (I') to (V), where $Q^1$ and $Q^2$ may also be OH, in vacuo for several hours, for example for from 1 to 10 hours, at from 40 to 60° C., or is dissolved in a suitable solvent, for example toluene or xylene, and the water is removed by azeotropic distillation.

The above-described intermediates of the formula (XX)

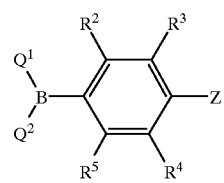

(XX)

in which Z is COHal, CO—NHNH$_2$ or

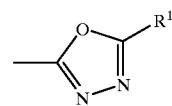

are novel and are likewise a subject-matter of the invention.

A major technical advantage of the process according to the invention is that the synthesis of the oxadiazole heterocycle can be carried out without salt waste and as a one-pot reaction. The compounds used for the protecting groups $Q^1$ and $Q^2$ can be recyclized.

EXAMPLES

Preparation Examples

Example 1

Esterification of 4-(carboxy)phenylboronic acid

4-Carboxyphenylboronic acid and an equimolar amount of the corresponding diol as shown in Table 1 are refluxed in 200 ml of toluene. When all the water formed has been removed on a water separator (after about 1 hour), the solution is filtered hot through a suction filter. The solvent is subsequently removed by distillation.

TABLE 1

| Diol | Amount of starting material | Product of the formula (V) | Yield |
|---|---|---|---|
| Pinacol | 30 g (180 mmol) | 4-(4,4,5,5-Tetramethyl-1,3,2-dioxaborolan-2-yl)-benzoic acid | 43.1 g (97%) |
| Neopentyl glycol | 16.6 g (100 mmol) | 4-(5,5-Dimethyl-1,3,2-dioxaborolan-2-yl)benzoic acid | 22 g (94%) |
| Ethylene glycol | 200 g (1.2 mol) | 4-(1,3,2-dioxaborolan-2-yl)benzoic acid | 227.1 g (98%) |
| Diethanolamine | 20 g (120 mmol) | 4-(1,3,6,2-Dioxazaborolan-2-yl)-benzoic acid | 27.5 g (98%) |

Example 2

Synthesis of compounds of the general formula (III) by Variant A

A suspension of a compound of the general formula (V) as shown in Table 1 in toluene is treated dropwise at the boil with an equimolar amount of thionyl chloride.

When the evolution of gas is complete, the mixture is boiled under reflux for a further 2 hours. The reaction mixture is subsequently treated with the equimolar amount of the alcohol $R^6OH$, for example methanol, and refluxed for a further 2 hours. The solvent is removed by distillation. Products and yields are shown in Table 2.

TABLE 2

| Starting material of the formula (V) | Amount | Product of the formula (III) | Yield |
|---|---|---|---|
| 4-(4,4,5,5-Tetramethyl-1,3,2-dioxaborolan-2-yl)-benzoic acid | 40 g (161 mmol) | Methyl 4-(4,4,5,5-tetramethyl-1,3,2-dioxaborolan-2-yl)benzoate | 36.4 g (86%) |
| 4-(5,5-Dimethyl-1,3,2-dioxaborolan-2-yl)-benzoic acid | 19 g (80 mmol) | Methyl 4-(5,5-dimethyl-1,3,2-dioxaborolan-2-yl)benzoate | 17.2 g (90%) |
| 4-(1,3,2-dioxaborolan-2-yl)benzoic acid | 10 g (52 mmol) | Methyl 4-(1,3,2-dioxaborolan-2-yl)benzoate | 9.4 g (88%) |

Example 2a

Variant D

Methyl 4-(4,4,5,5-tetramethyl-1,3,2-dioxaborolan-2-yl)benzoate 50 g (200 mmol) of 4-(4,4,5,5-tetramethyl-1,3,2-dioxaborolan-2-yl)benzoic acid and 1,22 g (10 mmol) of N,N-dimethylpyridine are dissolved in 200 ml of methanol and refluxed for 5 hours. Removal of 150 ml of methanol by distillation gives 43.4 g (165 mmol, 83%) of product.

Example 3

4-(4,4,5,5-Tetramethyl-1,3,2-dioxaborolan-2-yl)benzohydrazide 20 g (76 mmol) of methyl 4-(4,4,5,5-tetramethyl-1,3,2-dioxaborolan-2-yl)benzoate are dissolved in 150 ml of methanol, 6 g (120 mmol) of hydrazine hydrate are added, and the mixture is refluxed for 12 hours. Removal of 120 ml of methanol by distillation gives 19.8 g (75 mmol, 98%) of product. The compounds of the formula (III) are obtained analogously using the compounds shown in Table 3.

TABLE 3

| Starting material of the formula (III) | Amount | Product of the formula (II) | Yield |
|---|---|---|---|
| Methyl 4-(4,4,5,5-tetramethyl-1,3,2-dioxaborolan-2-yl)benzoate | 20 g (76 mmol) | 4-(4,4,5,5-Tetramethyl-1,3,2-dioxaborolan-2-yl)-benzohydrazide | 19.8 g (98%) |
| Methyl 4-(5,5-dimethyl-1,3,2-dioxaborolan-2-yl)-benzoate | 19.5 g (80 mmol) | 4-(5,5-Dimethyl-1,3,2-dioxaborolan-2-yl)-benzohydrazide | 18.2 g (93%) |
| Methyl 4-(1,3,2-dioxaborolan-2-yl)benzoate | 88 g | 4-(1,3,2-dioxaborolan-2-yl)-benzohydrazide | 79.0 g (90%) |

Example 4

2-[4-(4,4,5,5-Tetramethyl-1,3,2-dioxaborolan-2-yl)phenyl]-1,3,4-oxadiazole 10 g (38 mmol) of 2-[4-(4,4,5,5-tetramethyl-1,3,2-dioxaborolan-2-yl)-benzohydrazide are dissolved in 30 g (20 mmol) of triethyl orthoformate, and the mixture is heated to reflux. The ethanol formed during the reaction is continuously removed by distillation. After the mixture has cooled, the product crystallizes out, is filtered off and washed with a little ethanol. Yield: 8.7 g (32 mmol, 84%). An analogous procedure is carried out using the compounds of the formula (II) shown in Table 4.

TABLE 4

| Starting material of the formula (II) | Amount | Product of the formula (I') | Yield |
|---|---|---|---|
| 4-(4,4,5,5-Tetramethyl-1,3,2-dioxaborolan-2-yl)-benzohydrazide | 10 g (38 mmol) | 2-[4-(4,4,5,5-Tetramethyl-1,3,2-dioxaborolan-2-yl)-phenyl]-1,3,4-oxadiazole | 8.3 g (84%) |
| 4-(5,5-Dimethy-1,3,2-dioxaborolan-2-yl)-benzohydrazide | 11.3 g (46 mmol) | 2-[4-(5,5-Dimethyl-1,3,2-dioxaborolan-2-yl)phenyl]-1,3,4-oxadiazole | 11 g (93%) |

TABLE 4-continued

| Starting material of the formula (II) | Amount | Product of the formula (I') | Yield |
|---|---|---|---|
| 4-(1,3,2-dioxaborolan-2-yl)-benzohydrazide | 12 g (58 mmol) | 2-[4-(1,3,2-Dioxaborolan-2-yl) phenyl]-1,3,4-oxadiazole | 10.8 g (87%) |

Example 5

1,3,4-Oxadiazol-2-ylphenylboronic acid 66 g (256 mmol) of 2-[4-(5,5-dimethyl-1,3,2-dioxaborolan-2-yl)phenyl]-1,3,4-oxadiazol are suspended in 250 ml of 5% by weight acetic acid, and the mixture is stirred at room temperature for 24 hours. The product is filtered off, washed with water and suspended in THF. The suspension is refluxed for 3 hours. After cooling the product is filtered off, washed with a little cold THF and dried. Yield 46.6 g (245 mmol, 96%). An analogous procedure is carried out using the compounds of the formula (I') shown in Table 5.

TABLE 5

| Starting material of the formula (I') | Amount | Product of the formula (I) | Yield |
|---|---|---|---|
| 2-[4-(4,4,5,5-Tetramethyl-1,3,2-dioxaborolan-2-yl)-phenyl]-1,3,4-oxadiazole | 10 g (38 mmol) | 1,3,4-Oxadiazol-2-yl-phenylboronic acid | 6.8 g (94%) after 3 days at RT |
| 2-[4-(5,5-Dimethyl-1,3,2-dioxaborolan-2-yl)-phenyl]-1,3,4-oxadiazol | 66 g (256 mmol) | 1,3,4-Oxadiazol-2-yl-phenylboronic acid | 46.6 g (96%) |
| 2-[4-(1,3,2-dioxaborolan-2-yl)-phenyl]-1,3,4-oxadiazol | 15 g (70 mmol) | 1,3,4-Oxadiazol-2-yl-phenylboronic acid | 12.7 g (96%) |

Example 6

4-(5,5-Dimethyl-1,3,2-dioxaborolan-2-yl) benzohydrazide by Variant B 58.5 g (250 mmol) of 4-(5,5-dimethyl-1,3,2-dioxaborolan-2-yl)benzoic acid are dissolved in 250 ml of methanol, and 12.5 g (250 mmol) of hydrazine hydrate and 1.5 g (12.5 mmol) of 4-dimethylaminopyridine are added. The solution is refluxed for 12 hours. Removal of 200 ml of methanol by distillation gives 44.6 g (180 mmol, 72%) of product.

Example 7

2-[4-(4,4,5,5-Tetramethyl-1,3,2-dioxaborolan-2-yl) phenyl)]-1,3,4-oxadiazole by Variant E 46.8 g (200 mmol) of 4-(4,4,5,5-tetramethyl-1,3,2-dioxaborolan-2-yl)benzoic acid are refluxed for 6 hours together with 12 g (200 mmol) of formylhydrazine and 31 g (200 mmol) of phosphorus oxychloride. When the reaction is complete, the reaction mixture is poured into 10% strength by weight sodium hydrogencarbonate solution. The precipitate is filtered off and dried, giving 51.6 g (65%) of product.

What is claimed is:

1. Process for the preparation of para-oxadiazolylphenylboronic acid of the formula (I)

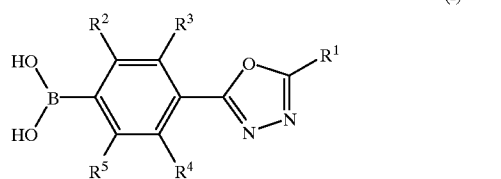

(I)

in which $R^1$ is hydrogen, $C_1$–$C_{12}$-alkyl, $C_3$–$C_{12}$-cycloalkyl, $C_2$–$C_{12}$-alkenyl, $C_2$–$C_{12}$-alkynyl, $C_1$–$C_{12}$-alkoxy, alkoxy-($C_1$–$C_{12}$-alkyl), alkoxy-($C_2$–$C_{12}$-alkenyl), alkoxy-($C_2$–$C_{12}$-alkynyl), acyloxy-($C_1$–$C_{12}$-alkyl), acyloxy-($C_2$–$C_{12}$-alkenyl), acyloxy-($C_2$–$C_{12}$-alkynyl), aryl, heteroaryl, OH, SH, F, Cl, Br, I or NR'R", where R' and R", independently of one another, are hydrogen, $C_1$–$C_{12}$-alkyl, $C_3$–$C_{12}$-cycloalkyl or aryl, $R^2$ to $R^5$, independently of one another, are hydrogen, $C_1$–$C_{12}$-alkyl, $C_2$–$C_{12}$-alkenyl, $C_2$–$C_{12}$-alkynyl, $C_3$–$C_{12}$-cycloalkyl, ($C_1$–$C_{12}$-)-alkoxy, ($C_1$–$C_{12}$)-acyloxy, O-phenyl, O-benzyl, aryl, heteroaryl, hydroxyl, fluorine, chlorine, bromine, iodine, nitro, CN, $SO_2R$ or SOR, where R is hydrogen, $C_1$–$C_4$-alkyl, aryl, chlorine or fluorine, or are $NH_2$, N(alkyl)$_2$, N[Si($C_1$–$C_4$-alkyl)$_3$]$_2$, $CF_3$, $CCl_3$, COO-($C_1$–$C_{12}$-alkyl), CO-($C_1$–$C_{12}$-alkyl), CO-phenyl, COO-phenyl, CHCHCOO-($C_1$–$C_2$-alkyl), PO-phenyl$_2$, PO-($C_1$–$C_8$-alkyl)$_2$ or PO$_3$($C_1$–$C_8$-alkyl)$_2$, or $R^2$ and $R^3$, $R^4$ and $R^5$, or both, together form an aliphatic or aromatic ring, wherein a compound of the formula (V)

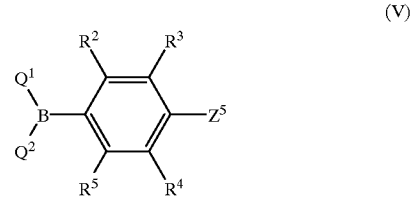

(V)

in which $Z^5$ is —COOH;

is reacted with a compound of the formula (X)

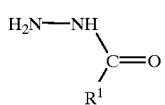
(X)

to give the compound of the formula (I')

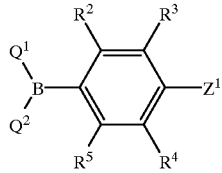
(I')

in which $Z^1$ is

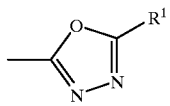

and the compound of the formula (I') is hydrolyzed to give the compound of the formula (I), or the compound of the formula (V) is firstly reacted with hydrazine to give a compound of the formula (II)

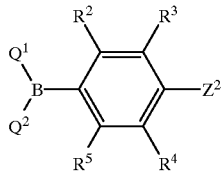
(II)

in which $Z^2$ is —CONHNH$_2$, and the compound of the formula (II) is cyclized and hydrolyzed;

where $Q^1$ and $Q^2$ are each a radical of the formula —O-($C_1$–$C_{12}$)-alkyl, —O-($C_2$–$C_{12}$)-alkenyl, —O-($C_2$–$C_{12}$)-alkynyl, —O-aryl, —O-alkylaryl or —O-Si($C_1$–$C_4$-alkyl)$_3$; or $Q^1$, $Q^2$ and the adjacent boron atom form a cyclic boronic ester with the following alcohols: ($C_3$–$C_{12}$)cycloalkane-1,2-diol, ($C_5$–$C_{12}$)-cycloalkene-1,2-diol, ($C_5$–$C_{12}$)-cycloalkane-1,3-diol, ($C_5$–$C_{12}$)-cycloalkene-1,3-diol or with alcohols of the formulae (Ia) to (If)

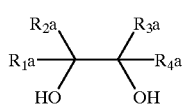
(Ia)

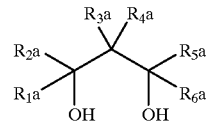
(Ib)

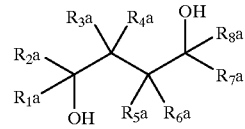
(Ic)

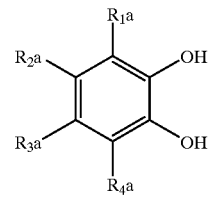
(Id)

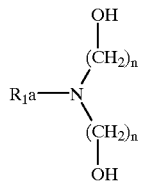
(Ie)

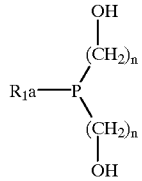
(If)

in which $R_1a$ to $R_8a$, independently of one another, are hydrogen, $C_1$–$C_{12}$-alkyl, $C_1$–$C_{12}$-hydroxyalkyl, $C_2$–$C_{12}$-alkenyl, $C_2$–$C_{12}$-alkynyl, $C_3$–$C_{12}$-cycloalkyl, ($C_1$–$C_{12}$)-alkoxy, ($C_1$–$C_{12}$)-acyloxy, O-phenyl, O-benzyl, aryl, heteroaryl, fluorine, chlorine, bromine, iodine, NO$_2$, CN, SO$_2$R, SOR, where R is as defined above, or are NH$_2$, N(alkyl)$_2$, N[Si($C_1$–$C_4$-alkyl)$_3$]$_2$, CF$_3$, CCl$_3$, CBr$_3$, COO-($C_1$–$C_{12}$-alkyl), CO-($C_1$–$C_{12}$-alkyl), CO-phenyl, COO-phenyl, CHCHCOO-($C_1$–$C_2$-alkyl), PO-phenyl$_2$, PO-($C_1$–$C_8$-alkyl)$_2$ or PO$_3$($C_1$–$C_8$-alkyl)$_2$, or two adjacent radicals $R_1a$ to $R_8a$ together form an aliphatic or aromatic ring, and in which n is an integer from 2 to 12, or in which $Q^1$ and $Q^2$ together form a divalent radical of the formula (Ig)

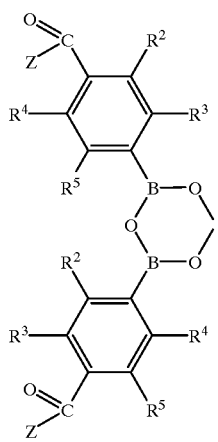

(Ig)

in which all radicals Z, in each case correspondingly, have one of the meanings of $Z^1$ to $Z^5$.

2. Process according to claim 1, characterized in that the compound of the formula (II) is prepared by reacting the compound of the formula (V) with hydrazine hydrate in the presence of an esterification catalyst at a temperature of from 0 to 200° C.

3. Process according to claim 1, characterized in that the compound of the formula (II) is prepared by esterifying the compound of the formula (V) using an alcohol of the formula $R^6OH$, in which $R^6$ is $C_1$–$C_{12}$-alkyl, $C_2$–$C_{12}$-alkenyl, $C_3$–$C_{12}$-cycloalkyl, $CF_3$, $CCl_3$, $CBr_3$, phenyl, benzyl, naphthyl, heteroaryl, $C_1$–$C_{12}$-hydroxyalkyl or $C_2$–$C_{12}$-hydroxyalkenyl, to give the compound of the formula (III)

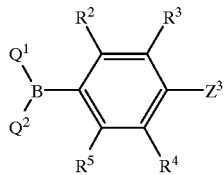

(III)

in which $Z^3$ is —$COOR^6$,
and reacting the compound of the formula (III) with hydrazine hydrate.

4. Process according to claim 1, characterized in that the compound of the formula (II) is prepared by halogenating the compound of the formula (V) using thionyl chloride, phosphorus(V) chloride or phosphorus(III) chloride to give the compound of the formula (IV)

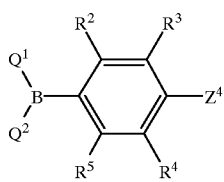

(IV)

in which $Z^4$ is —COHal, where Hal is Cl, Br or I,
and reacting the compound of the formula (IV) with hydrazine hydrate; or esterifying the compound of the formula (IV) using an alcohol of the formula $R^6OH$, where $R^6$ is $C_1$–$C_{12}$-alkyl, $C_2$–$C_{12}$-alkenyl, $C_3$–$C_{12}$-cycloalkyl, $CF_3$, $CCl_3$, $CBr_3$, phenyl, benzyl, naphthyl, heteroaryl, $C_1$–$C_{12}$-hydroxyalkyl or $C_2C_{12}$-hydroxyalkenyl.

5. Process according to claim 1, characterized in that the compound of the formula (II) is cyclized at a temperature of from 0 to 200° C. and in the presence of an orthocarboxylic ester to give the compound of the formula (I').

6. Process according to claim 1, characterized in that the compound of the formula (V) is reacted with the compound of the formula (X) at a temperature of from 50 to 250° C.

7. Process according to claim 1, characterized in that $R^1$ is hydrogen, $C_1$–$C_4$-alkyl, $C_3$–$C_6$-cycloalkyl, $C_2$–$C_4$-alkenyl, phenyl, $NH_2$, OH, SH or $C_1$–$C_4$-alkoxy.

8. Process according to claim 1, characterized in that the radicals $R^2$ to $R^5$ are identical or different and are hydrogen, methyl, ethyl, methoxy, ethoxy, fluorine, chlorine or bromine.

9. Process according to claim 1, characterized in that the radicals $Q^1$ and $Q^2$ are —O-($C_1$–$C_6$)-alkyl, —O-($C_2$–$C_6$)-alkenyl, —O-($C_3$–$C_6$)-alkynyl, —O-phenyl or —O-benzyl, or $Q^1$ and $Q^2$ together with the boron atom, form a cyclic boronic ester with the following alcohols:

ethylene glycol, 1,3-propanediol, 1,4-butanediol, 2,2-dimethylpropane-1,3-diol, pyrocatechol, pinacol, 2,3-dihydroxynaphthalene, diethanolamine, triethanolamine, trishydroxymethyl-phosphine, 1,2-dihydroxycyclohexane, 1,3-dihydroxycyclopentane or 1,2-dihydroxycyclooctane.

10. Compound of the formula (XX)

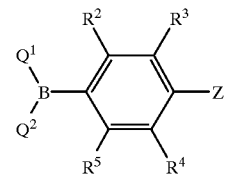

(XX)

in which Z is —COHal; CO—$NHNH_2$ or

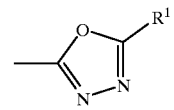

20 and $R^1$ to $R^5$, where $Q^1$ and $Q^2$ are each a radical of the formula —O-($C_1$–$C_{12}$)-alkyl, —O-($C_2$–$C_{12}$)alkenyl, —O-($C_2$–$C_{12}$)-alkynyl, —O-aryl, —O-alkylaryl or —O-Si($C_1$–$C_4$-alkyl)$_3$; or $Q^1$, $Q^2$ and the adjacent boron atom form a cyclic boronic ester with the following alcohols:

$C_3$–$C_{12}$)-cycloalkane-1,2-diol, ($C_5$–$C_{12}$)-cycloalkene-1,2-diol, ($C_5$–$C_{12}$)-cycloalkane-1,3-diol, ($C_5$–$C_{12}$)-cycloalkene-1,3-diol or with alcohols of the formulae (Ia) to (If)

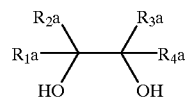

(Ia)

-continued

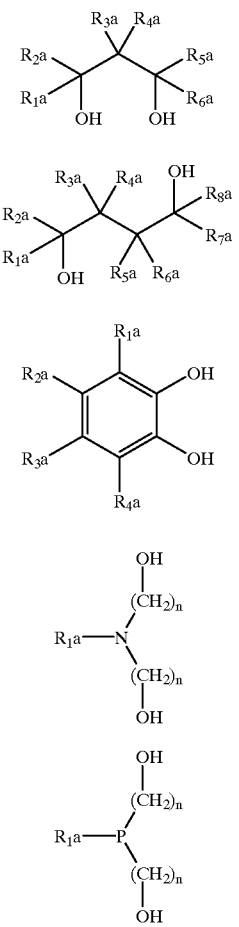

in which $R_1a$ to $R_8a$, independently of one another, are hydrogen, $C_1$–$C_{12}$-alkyl, $C_1$–$C_{12}$-hydroxyalkyl, $C_2$–$C_{12}$-alkenyl, $C_2$–$C_{12}$-alkynyl, $C_3$–$C_{12}$-cycloalkyl, $(C_1$–$C_{12})$-alkoxy, $(C_1$–$C_{12})$-acyloxy, O-phenyl, O-benzyl, aryl, heteroaryl, fluorine, chlorine, bromine, iodine, $NO_2$, CN, $SO_2R$, SOR, where R is as defined above, or are $NH_2$, N(alkyl)$_2$, N[Si$(C_1$–$C_4$-alkyl)$_3]_2$, $CF_3$, $CCl_3$, $CBr_3$, COO-$(C_1$–$C_{12}$-alkyl), CO-$(C_1$–$C_{12}$-alkyl), CO-phenyl, COO-phenyl, CHCHCOO-$(C_1$–$C_2$-alkyl), PO-phenyl$_2$, PO-$(C_1$–$C_8$-alkyl)$_2$ or $PO_3(C_1$–$C_8$-alkyl)$_2$, or two adjacent radicals $R_1a$ to $R_8a$ together form an aliphatic or aromatic ring, and in which n is an integer from 2 to 12, or in which $Q^1$ and $Q^2$ together form a divalent radical of the formula (Ig)

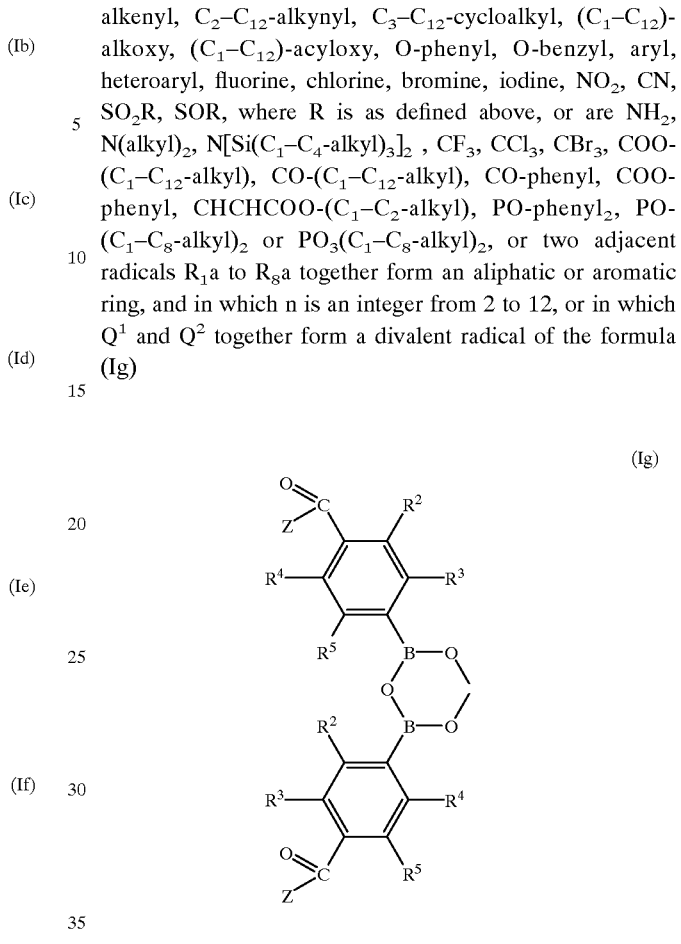

in which all radicals Z, in each case correspondingly, have one of the meanings of $Z^1$ to $Z^5$.

* * * * *